(12) United States Patent
Collins et al.

(10) Patent No.: US 6,613,053 B1
(45) Date of Patent: Sep. 2, 2003

(54) SURGICAL IMPLANT

(75) Inventors: Simon Nicholas Collins, Gloucestershire (GB); David Mark Fletcher, Gloucestershire (GB)

(73) Assignee: Corin Limited, Cirencester (GB)

( * ) Notice: Subject to any disclaimer, the term of this patent is extended or adjusted under 35 U.S.C. 154(b) by 0 days.

(21) Appl. No.: 10/192,324

(22) Filed: Jul. 11, 2002

(30) Foreign Application Priority Data

Oct. 25, 2001 (GB) .............................................. 0125565

(51) Int. Cl.[7] .............................................. A61B 17/56
(52) U.S. Cl. .............................. 606/69; 606/61; 606/73
(58) Field of Search .............................. 606/69, 73, 72, 606/61, 65, 60, 70, 71

(56) References Cited

U.S. PATENT DOCUMENTS

| | | | |
|---|---|---|---|
| 5,489,210 A | * 2/1996 | Hanosh ........................ 433/173 |
| 5,569,251 A | * 10/1996 | Baker et al. ................... 606/69 |
| 5,713,900 A | * 2/1998 | Benzel et al. .................. 606/61 |
| 5,843,082 A | * 12/1998 | Yuan et al. .................... 606/61 |
| 6,036,693 A | * 3/2000 | Yuan et al. .................... 606/61 |
| 6,168,597 B1 | * 1/2001 | Biedermann et al. ......... 606/73 |
| 6,235,033 B1 | 5/2001 | Brace et al. |

FOREIGN PATENT DOCUMENTS

EP              0 809 974 A2       12/1997

* cited by examiner

*Primary Examiner*—Pedro Philogene

(57) ABSTRACT

A surgical implant, typically a cervical plate assembly, comprises a plate having at least two apertures and two screw threaded fastening devices for securing the plate to bone. Each aperture in the plate has an annular groove intermediate opposite ends of the aperture and each fastening device comprises an outer screw and an inner plug. The screw has a head at one end, a tip at the other end, an externally threaded shank between the head and the tip and an internal bore extending axially through the head and at least part way into the shank for receiving the inner plug. The head comprises a plurality of resiliently deformable fingers separated by one another by axially extending slits. Each finger has an outwardly projecting rib extending circumferentially of the head intermediate opposite ends of the finger for snap fit engagement in the annular groove of a respective plate aperture. The inner plug is arranged so that when it is inserted into the internal bore of the screw it will prevent contraction of the head of the screw thereby preventing the ribs disengaging from the groove.

12 Claims, 3 Drawing Sheets

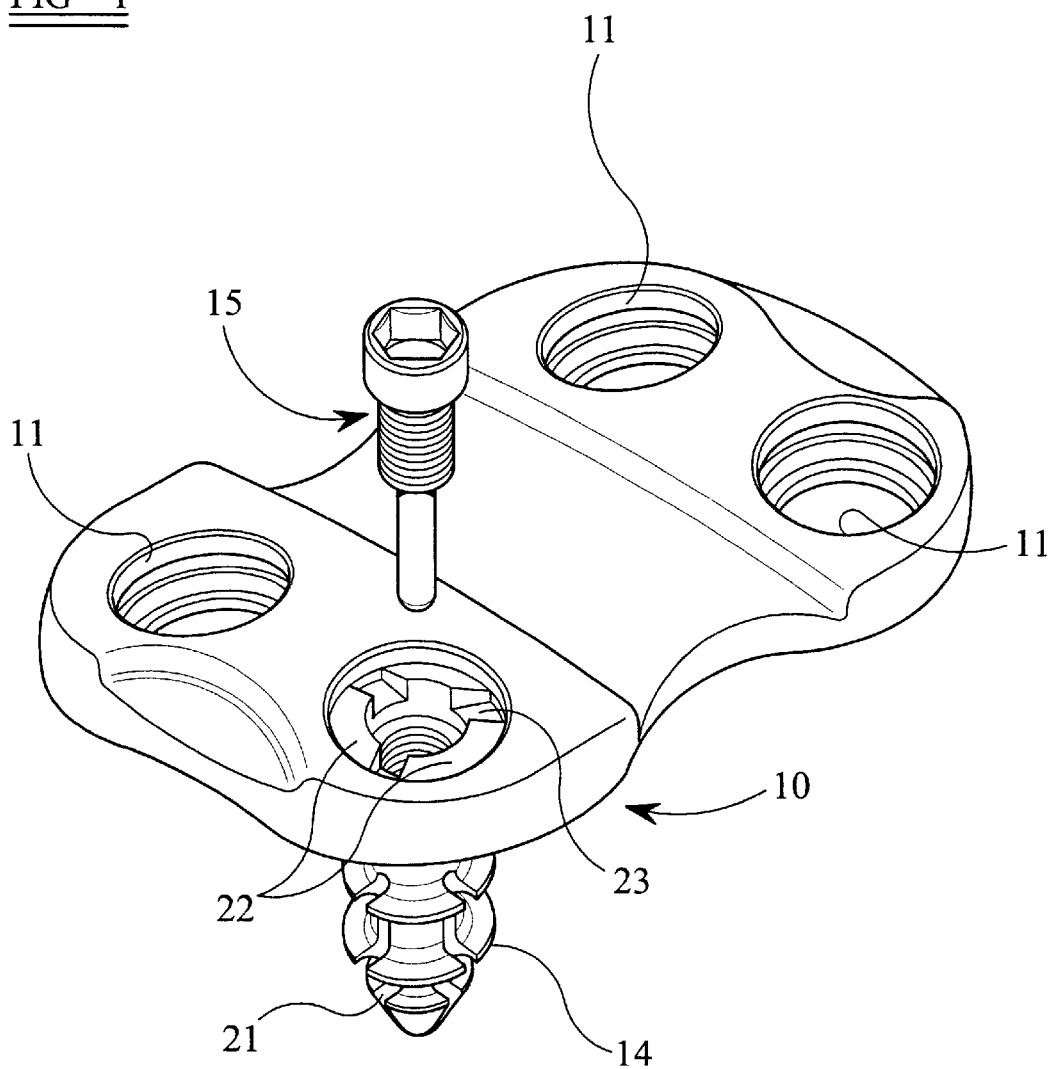

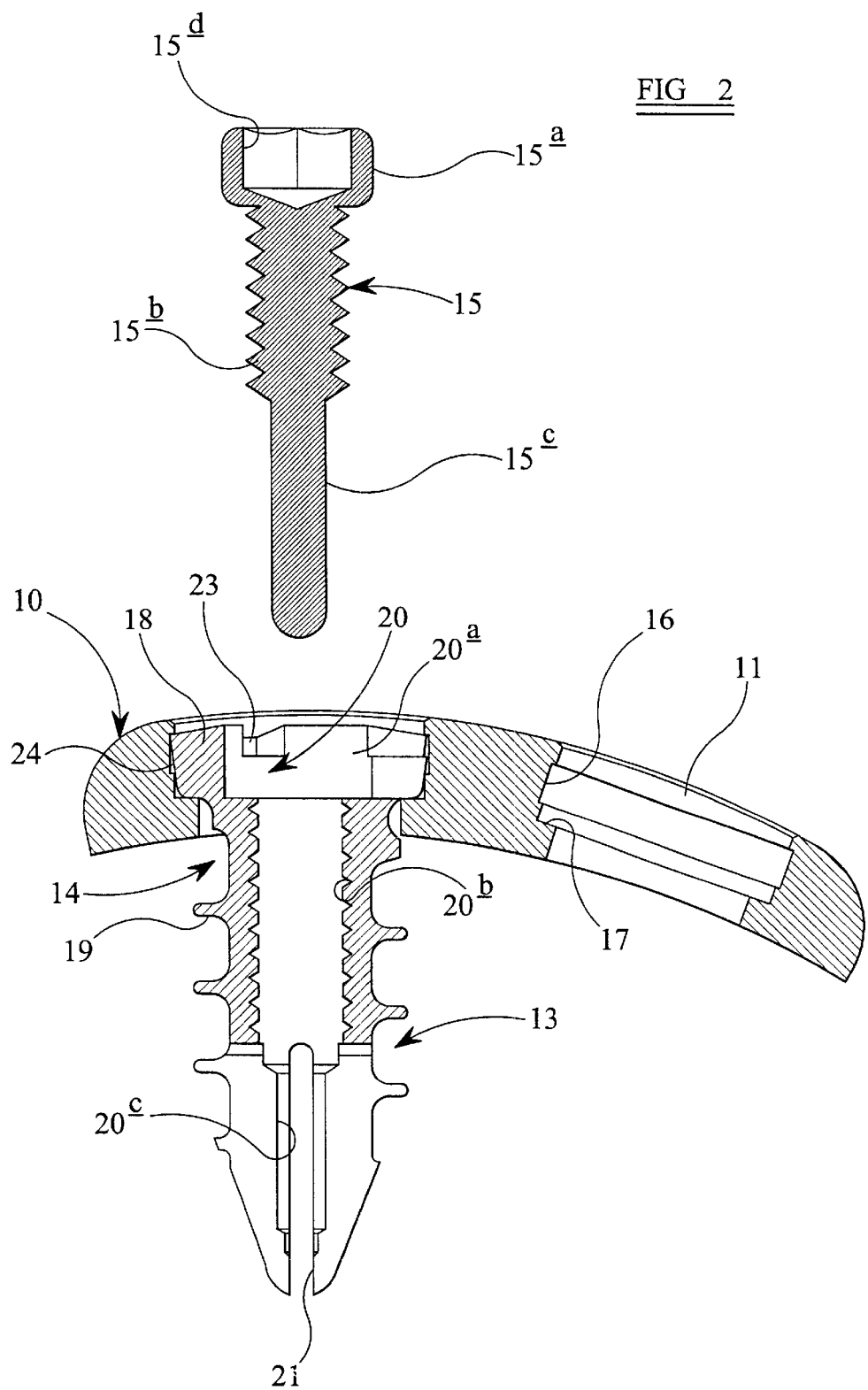

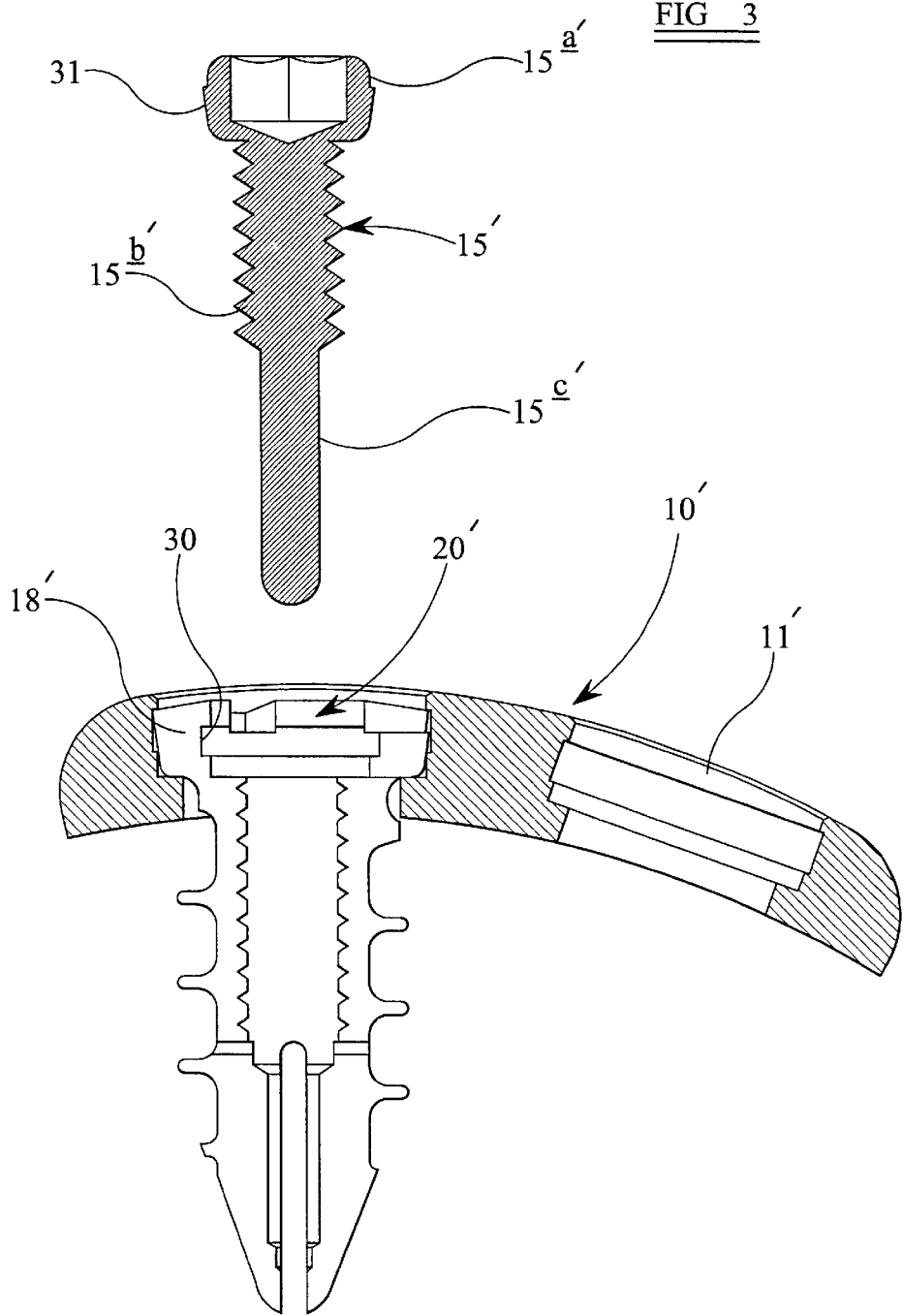

SURGICAL IMPLANT

This invention relates to a surgical implant and more particularly, but not exclusively, to a cervical plate assembly for stabilising the cervical spine.

Plates are commonly used to connect two separated pieces of bone. These plates immobilise the broken bone pieces while the bone pieces fuse together. Cervical plates are commonly used for anterior spine stabilisation to assist fusion in cases of degenerative disease, tumours, fractures and partial or total vertebrectomy. The plates are fixed to the bone by screws. It is known to provide the screws with expansion cones to expand the tip of the screw after insertion of the latter in the bone. This results in secure fixation. However, it is often difficult.in young patients or in good quality bone to expand the tip of the screw.

It is known from U.S. Pat. No. 4,484,570 to expand the head of the screw to provide secure fixation of the screw to the plate. However, this suffers from the disadvantage that a force arises from the tapered mating of the inner and outer screws which may contribute to loosening and subsequent screw pull out leading to failure of the device.

SUMMARY OF THE INVENTION

According to the present invention there is provided a surgical implant comprising a plate having at least two apertures and two screw threaded fastening devices for securing the plate to bone, each aperture in the plate having an annular groove intermediate opposite ends of the aperture and each fastening device comprising an outer screw and an inner plug, the screw having a head at one end, a tip at the other end, an externally threaded shank between the head and the tip and an internal bore extending axially through the head and at least part way into the shank for receiving the inner plug, the head comprising a plurality of resiliently deformable fingers separated from one another by axially extending slits, each finger having an outwardly projecting rib extending circumferentially of the head intermediate opposite ends of the finger for snap fit engagement in the annular groove of a respective plate aperture, and the inner plug being arranged so that when it is inserted into the internal bore of the screw it will prevent contraction of the head of the screw thereby preventing the ribs disengaging from the groove.

The invention will now be more particularly described, by way of example, with reference to the accompanying drawings.

BRIEF DESCRIPTION OF THE DRAWINGS

FIG. 1 is a perspective, partially exploded, view of one embodiment of a surgical implant according to the present invention, FIG. 2 is a section taken through FIG. 1, and FIG. 3 is a view similar to FIG. 2 of a second embodiment.

DESCRIPTION OF THE PREFERRED EMBODIMENT

Referring to the drawings, the surgical implant shown therein is in the form of a cervical plate assembly used for stabilising the cervical spine of a patient. The assembly comprises a cervical plate 10 having an aperture 11 adjacent each corner. It may also have a central aperture (not shown) to allow attachment of a bone graft to aid fusion. The plate 10 is of contoured non-planar shape and is available in various sizes so that a surgeon can select an appropriate plate which will not result in penetration of the intervertebral disc space by the fastening devices referred to below.

The assembly comprises four screw threaded fastening devices 13 for securing the plate 10 to bone. Each fastening device 13 comprises an outer screw 14 and an inner plug 15.

Each aperture 11 in the plate has an annular groove 16 intermediate the outer and inner ends of the aperture and an annular ledge 17 between the annular groove 16 and the inner end of the aperture 11.

Each outer screw 14 comprises a head 18, an externally threaded shank 19 and an internal bore 20 extending axially through the head 18 and through the shank 19 for receiving the plug 15.

The bore 20 has a first portion 20a in the head 18 of the screw 14, a second portion 20b extending into the shank 19 from the portion 20a and a third portion 20c extending from the portion 20b through the tip of the screw 13. The portion 20b is of larger diameter than the portion 20c and the portion 20a is of larger diameter than the portion 20b. The portion 20b of the bore 20 is internally screw threaded for a purpose which will become apparent.

The tip of the screw 13 has four equi-angularly spaced, axially extending slits 21 which allow the tip to be outwardly deformed in a manner to be described hereinafter.

The plug 15 has a head portion 15a which is a close fit in the portion 20a of the bore 20, an externally threaded shank 15b which threadably engages the portion 20b of the bore 20 and an expansion element 15c of slightly larger diameter than the portion 20c of the bore 20 for outwardly deforming the tip end of the screw 14.

The tip of the expansion element 15c is tapered or part spherical in order to assist insertion of the expansion element 15c into the bore portion 20c.

The head 18 of the screw 14 comprises a plurality of resiliently deformable fingers (in this case three) 22 separated from one another by axially extending slits 23. Each finger 22 has an outwardly projecting rib 24 extending circumferentially of the head 18 intermediate opposite ends of the finger 22 for snap fit engagement in the annular groove 16 of a plate aperture 11. As shown, the rib 24 is inwardly tapered towards the tip of the screw but this need not necessarily be the case.

The head portion 15a of the plug 15 has a non-circular, and as shown hexagonal, socket 15d for receiving an insertion tool.

In order to fix the cervical plate assembly to the cervical spine, the outer screws 14 are screwed into bone through the apertures 11 by a known tubular screw driver until the head 18 of the screw 14 abuts the ledge 17 in the aperture and the ribs 24 snap fittably engage in the groove 16. The plug 15 is then inserted and screwed into place by a hexagonal screw driver inserted through the tubular screw driver, the latter acting as a guide and preventing the screw 14 from turning during insertion of the plug 15. When the plug 15 is fully in place, the head 15a of the plug is a close fit in the portion 20a of the bore 20 in the screw and this prevents contraction of the head 18 of the screw thereby preventing the ribs 24 disengaging from the groove 16. Also, the expansion element 15c expands the tip of the screw 13 to improve the overall fixation and prevent pull out of the fastening devices.

In some circumstances, it will be difficult to expand the tip of the screw 13 and in such cases a different plug having no expansion element will be used.

The plate 10, screws 14 and plugs 15 are made of suitable biocompatible material, typically commercially pure or alloyed titanium.

The embodiment shown in FIG. 3 differs from that shown in FIG. 2 in that the portion 20a of the bore 20 in the screw has an annular groove 30 to receive an annular rib 31 on the head 15a of the plug 15 as a snap fit.

The implant described above is in the form of a cervical plate assembly. However, the invention is equally applicable to any plates used to immobilise broken bone pieces. Thus, the plate may take other forms and may, for example, have only two apertures.

The embodiments described above are given by way of example only and various modifications will be apparent to persons skilled in the art without departing from the scope of the invention as defined by the appended claims. For example, the plug could be a push fit in the bore of the screw.

What is claimed is:

1. A surgical implant comprising a plate having at least two apertures and two screw threaded fastening devices for securing the plate to bone, each aperture in the plate having an annular groove intermediate opposite ends of the aperture and each fastening device comprising an outer screw and an inner plug, the screw having a head at one end, a tip at the other end, an externally threaded shank between the head and the tip and an internal bore extending axially through the head and at least part way into the shank for receiving the inner plug, the head comprising a plurality of resiliently deformable fingers separated from one another by axially extending slits, each finger having an outwardly projecting rib intermediate opposite ends of the finger for snap fit engagement in the annular groove of a respective plate aperture, and the inner plug being arranged so that, when it is inserted into the internal bore of the screw, it will prevent contraction of the head of the screw thereby preventing the ribs disengaging from the groove.

2. A surgical implant as claimed in claim 1, wherein the plug comprises a head which is a close fit in that part of the internal bore extending through the head of the screw and an externally threaded shank which is screw threadably engageable with an internal thread on at least part of the bore in the shank of the screw.

3. A surgical implant as claimed in claim 1, wherein each plate aperture has an annular ledge between the annular groove and the inner end of the aperture for engagement by the inner end of the screw head when the ribs are in snap fit engagement with the annular groove.

4. A surgical implant as claimed in claim 1, wherein the head of the plug has a noncircular socket for receiving a tool for inserting the plug in the internal bore of the screw.

5. A surgical implant as claimed in claim 1, wherein the internal bore extends throughout the entire length of the screw, the tip end of the screw being outwardly deformable and the tip end of the plug including an expansion element for outwardly deforming the tip end of the screw as the plug is inserted in the internal bore.

6. A surgical implant as claimed in claim 5, wherein the tip end of the screw has a plurality of axially extending slits.

7. A surgical implant as claimed in claim 1, wherein each rib is tapered inwards towards the tip of the screw.

8. A surgical implant as claimed in claim 1, wherein the plug is snap fittably engageable in the screw.

9. A surgical implant as claimed in claim 1, wherein the plate is a cervical plate.

10. A surgical implant as claimed in claim 9, wherein the plate has at least four apertures.

11. A surgical implant as claimed in claim 9, wherein the plate is non-planar.

12. A surgical implant as claimed in claim 8, wherein the plug comprises a head having an annular rib and the screw comprises an annular groove in the internal bore to receive the annular rib.

* * * * *